United States Patent
Benazzi et al.

(10) Patent No.: US 6,191,333 B1
(45) Date of Patent: *Feb. 20, 2001

(54) PROCESS FOR ISOMERIZATION OF NORMAL C5-C10 PARAFFINS USING BRIDGED LONG-RETICULATE-DISTANCE DIOCTAHEDRAL PHYLLOSILICATE 2:1

(75) Inventors: Eric Benazzi, Chatou; Jocelyne Brendle, Wittenheim; Ronan Le Dred, Riedisheim; Jacques Baron, Mulhouse; Daniel Saehr, Riedisheim, all of (FR)

(73) Assignee: Institut Francais du Petrole (FR)

( * ) Notice: Under 35 U.S.C. 154(b), the term of this patent shall be extended for 0 days.

This patent is subject to a terminal disclaimer.

(21) Appl. No.: 09/198,606

(22) Filed: Nov. 24, 1998

(30) Foreign Application Priority Data

Nov. 25, 1997 (FR) .................................................. 97 14889

(51) Int. Cl.⁷ ...................................................... C07C 5/13
(52) U.S. Cl. .......................... 585/749; 587/739; 587/748; 587/750; 502/63; 502/80; 502/84; 502/85
(58) Field of Search ................................. 502/80, 84, 85, 502/63; 585/739, 748, 749, 750

(56) References Cited

U.S. PATENT DOCUMENTS

| | | | |
|---|---|---|---|
| 4,436,832 | * 3/1984 | Jacob et al. | 502/84 |
| 4,757,040 | * 7/1988 | Guan et al. | 502/63 |
| 4,766,099 | * 8/1988 | Dufresne et al. | 502/72 |
| 5,059,568 | * 10/1991 | McCauley | 502/65 |
| 5,389,593 | 2/1995 | Holmgren | 502/63 |
| 5,414,185 | * 5/1995 | Salem et al. | 585/721 |

FOREIGN PATENT DOCUMENTS

| | | |
|---|---|---|
| 0 341 023 | 11/1989 | (EP) . |
| 0 505 005 | 10/1992 | (EP) . |
| 88/000091 | 1/1988 | (WO) . |

* cited by examiner

Primary Examiner—Tom Dunn
(74) Attorney, Agent, or Firm—Millen, White, Zelano & Branigan, P.C.

(57) ABSTRACT

This invention pertains to the use of a catalyst that contains at least one dioctahedral phyllosilicate 2:1, which is preferably synthesized in a fluoride medium in the presence of HF acid and/or another source of fluoride anions, whose reticulate distance is equal to at least $20 \times 10^{-10}$ m (2 nm) and which includes pillars that are based on at least one oxide from the elements of groups IVB, VB, VIB, VIII, IB, IIB, IIA, IVA, or any combination of these oxides, and preferably selected from the group composed of $SiO_2$, $Al_2O_3$, $TiO_2$, $ZrO_2$, and $V_2O_5$, or any combination of the latter and at least one element from group VIII, in a process for isomerization of a feedstock that contains mainly normal paraffins that carry 5 to 10 carbon atoms per molecule.

28 Claims, No Drawings

PROCESS FOR ISOMERIZATION OF NORMAL C5-C10 PARAFFINS USING BRIDGED LONG-RETICULATE-DISTANCE DIOCTAHEDRAL PHYLLOSILICATE 2:1

FIELD OF THE INVENTION

This invention pertains to a process for isomerization, in the presence of hydrogen (also called a hydro-isomerization process), of normal C5–C10 paraffins using a long-reticulate-distance dioctahedral phyllosilicate 2:1 (sometimes also referred to as bridged clay).

The isomerization of normal paraffins that contains between 5 and 10 carbon atoms per molecule is currently of considerable importance in the petroleum industry, mainly in connection with the elimination of lead alkyls from gasolines.

At the present time, moreover, the specifications for gasoline fractions are becoming more stringent as regards their contents of aromatics. Reducing the amount of aromatics present in gasolines, taking into account the availability of the various gasoline fractions would mean reducing the octane rating, which would have to be offset. One possible way of limiting the octane loss would consist in isomerizing the linear paraffins having seven or eight carbon atoms, without aromatizing them. This transformation would allow a significant improvement in octane rating: n-heptane has an octane rating of 0, while that of methylhexanes is approximately 47, and that of dimethylpentanes is approximately 87.

Based on the number of carbon atoms that are present in the linear paraffins that are to be isomerized, different types of catalyst have been developed:

In the case of the isomerization (also called hydro-isomerization) of short linear paraffins that contain 4 to 6 carbon atoms per molecule, catalysts of the Friedel and Crafts types, such as aluminum chloride, are used at low temperatures (approximately 80–130° C.), as well as catalysts that contain at least one metal from group VIII supported on a halogenated, preferably chlorinated, base, which are used at moderate temperatures (approximately 150° C.). Nonetheless, the selectivity of these catalysts in terms of isomerized products turns out to be inadequate in the case of the isomerization of longer C6+ paraffins (paraffins having more than six carbon atoms per molecule).

Many patents have as their objects zeolitic catalysts or molecular sieves that contain at least one metal from group VIII deposited on a zeolite; said catalysts are used at high temperatures (220° C. or more) and in the presence of hydrogen. In the case of linear paraffins with 5 and 6 carbon atoms per molecule, said catalysts lead to smaller improvements in octane in the products that are produced than the two kinds of catalysts described above, but they have the advantage of being easier to use and more resistant to poisons. By way of example of the hydro-isomerization of paraffins on zeolites, the catalysts based on mordenite and a hydro-dehydrogenating element are described in patents U.S. Pat. No. 3,432,568 and U.S. Pat. No. 3,673,267. Or, more recently, patents EP-398416 and WO 96/18705, which claim the use of catalysts based on Beta zeolites (BEA) and at least one hydro-dehydrogenating metal, in the presence of hydrogen, in order to carry out the hydro-isomerization of short paraffins.

The isomerization (hydro-isomerization) of linear paraffins having 4 to 8 carbon atoms per molecule can also be carried out with bifunctional catalysts that combine an acid function with a hydro-dehydrogenating function. With this kind of catalyst, the main parasitic reactions are cracking, hydrogenolysis, aromatization, and coking.

The catalysts that are described above for the isomerization (hydro-isomerization) of short linear paraffins (having 4 to 6 carbon atoms per molecule) have also been used in the hydro-isomerization of C7 and C8 paraffins, but these catalysts provide isomerized-product yields that are still inadequate.

Non-zeolitic molecular sieves (SAPO, silico-aluminophosphates) with shape selectivity have also been claimed, patents U.S. Pat. No. 5,114,563 and U.S. Pat. No. 4,710,485, for the purpose of ensuring the selective hydro-isomerization of C7 to C20 linear paraffins. These molecular sieves, which have acidity levels that are much sweeter than zeolites, lead to higher yields of isomerized products. As a matter of fact, it has been noted that cracking reactions, secondary reactions, are of less significance when these solids are used as isomerization catalysts. Nevertheless, these solids have activity levels that are lower; this makes it necessary to work with them at higher temperatures than with zeolite-based catalysts. However, thermodynamics teaches us that any increase in the reaction temperature leads to a reduction in the percentage of multi-branched products in the reaction products, and hence to a smaller gain in octane rating.

SUMMARY OF THE INVENTION

The work that has been done has led us to show that, surprisingly, a catalyst that contains at least one dioctahedral phyllosilicate 2:1, which is preferably synthesized in a fluoride medium in the presence of HF acid and/or another source of fluoride anions, whose reticulate distance is equal to at least $20 \times 10^{-10}$ m (or 2 nanometers or 2 nm) and which includes pillars based on at least one oxide from the elements of groups IVB, VB, VIB, VIII, IB, IIB, IIA, IVA, or any combination of these oxides, and preferably selected from the group composed of $SiO_2$, $Al_2O_3$, $TiO_2$, $ZrO_2$ and $V_2O_5$, or any combination of said oxides, makes it possible to achieve an isomerized-product (hydro-isomerized product) selectivity that is better than that of the catalysts known in the prior art and even, in certain cases, with a higher level of activity.

This invention therefore pertains to the use of a catalyst that contains at least one dioctahedral phyllosilicate 2:1, which is preferably synthesized in a fluoride medium in the presence of HF acid and/or another source of fluoride anions, whose reticulate distance is equal to at least $20 \times 10^{-10}$ m (2 nm) and which includes pillars based on at least one oxide from the elements of groups IVB, VB, VIB, VIII, IB, IIB, IIA, IVA, or any combination of these oxides, and preferably selected from the group composed of $SiO_2$, $Al_2O_3$, $TiO_2$, $ZrO_2$, and $V_2O_5$, or any combination of the latter and at least one element from group VIII, in a conventional process for isomerization of a feedstock that contains mainly normal paraffins that carry 5 to 10 carbon atoms per molecule and preferably 5 to 8 carbon atoms per molecule, whose normal operating conditions are presented below.

More accurately, the catalyst contains at least one dioctahedral phyllosilicate 2:1 whose reticulate distance is equal to at least $20 \times 10^{-10}$ m (2 nm) and which includes pillars based on at least one oxide from the elements of groups IVB, VB, VIB, VIII, IB, IIB, IIA, IVA, or any combination of these oxides, and preferably selected from the group composed of $SiO_2$, $Al_2O_3$, $TiO_2$, $ZrO_2$, and $V_2O_5$, or any combination of the latter, at least one matrix, and at least one hydro-dehydrogenating element from group VIII that is selected from the group composed of: Fe, Co, Ni, Ru, Rh, Pd, Os, Ir, and Pt. The dioctahedral phyllosilicates 2:1 (which are preferably prepared in advance in a fluoride medium in the presence of HF acid and/or another source of fluoride anions) which are preferably bridged by the process described below, have a reticulate distance $d_{001}$ that is equal to least $20 \times 10^{-10}$ m (2 nm), preferably equal to least $26.5 \times 10^{-10}$ m, and even more preferably equal to least $28 \times 10^{-10}$ m, and most preferably equal to least $30 \times 10^{-10}$ m. Said reticulate distance is generally less than or equal to $60 \times 10^{-10}$ m, and preferably less than or equal to $50 \times 10^{-10}$ m. Said reticulate distance, which is represented by $d_{001}$, represents the sum of the thickness of a sheet and the inter-sheet space. This value is directly accessible by the method that is familiar to one skilled in the art of x-ray fraction on oriented powder.

Dioctahedral phyllosilicates 2:1 are minerals that are produced by the stacking of elementary sheets. Even though the chemical bonds between the elements of the structure of the phyllosilicates are ionocovalent, said bonds will be assumed to be ionic in order to simplify the description.

Starting from a representation where the $O^{2-}$ ions are in a plane in contact with one another, it is possible to obtain a plane that represents a hexagonal cavity, called a hexagonal plane, by removing every other $O^{2-}$ ion in every other row of $O^{2-}$ ions.

The structure of a phyllite can be simply represented starting from arrangements of hexagonal planes of $O^{2-}$ ions and compact planes of $O^{2-}$ and $OH^-$ ions. The $OH^-$ ions fill the cavities in the hexagonal planes of $O^{2-}$ ions.

The superposition of two compact planes that are framed on both sides by a hexagonal plane makes it possible to define an octahedral layer (O) between two tetrahedral (T) layers, hence the name TOT sheets.

Such an arrangement, which is also referred to as 2:1, makes it possible to define an octahedral-cavity plane that is located in the octahedral layer between two tetrahedral-cavity planes, one in each tetrahedral layer. Each tetrahedron has one $O^{2-}$ ion in common with the octahedral layer, and each of the three other $O^{2-}$ ions is shared with another tetrahedron in the same tetrahedral layer.

The crystalline mesh (unit cell) is thus composed of 6 octahedral cavities that have 4 tetrahedral cavities on both sides. In the case of a phyllite that is composed of the elements Si, Al, O, and H, such an arrangement corresponds to the ideal formula $Si_8 (Al_4\square_2)O_{20} (OH)_4$. The tetrahedral cavities contain the element silicon, and the octahedral cavities contain the element aluminum, but in this case one octahedral cavity out of three is empty ($\square$). Such a unit is electrically neutral. Use is often made of the unit cell, whose formula is:

$$Si_4(Al_2\square)O_{10} (OH)_2$$

The element tetrahedral silicon can be replaced by trivalent elements such as, for example, aluminum, gallium, or iron ($Fe^{3+}$). Likewise, the element octahedral aluminum can be replaced by:

the above-mentioned trivalent elements, or a mixture of said elements;

divalent elements (Mg).

These substitutions impart negative charges to the structure. Said substitutions account for the existence of exchangeable compensation cations located in the inter-sheet space. The thickness of the inter-sheet space depends on the nature of the compensation cations and their state of hydration. This space is also able to accommodate other kinds of chemicals such as water, amines, salts, alcohols, bases, etc. . . .

The existence of —OH groups causes thermal instability due to the dehydroxylation reaction having the equation: 2 —OH →—O—+$H_2O$. In this connection, the introduction during the synthesis process of the element fluorine into the structure in place of the O—H groups produces phyllosilicates with considerably improved thermal stability.

The general chemical formula (for a unit cell) of dioctahedral phyllosilicates 2:1, which are preferably synthesized in a fluoride medium in the presence of HF acid and/or another source of fluorine anions before bridging, is as follows:

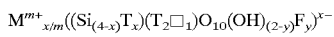

where:

T represents an element that is selected from the complex that is formed by the elements of group IIIA (such as, for example, B, Al, Ga) and iron;

M is at least one compensation cation that is selected from the group that is formed by the cations of the elements of groups IA, IIA, and VIII, the organic cations containing nitrogen, the ammonium cation, and the cations of the rare earths. The cation comes from the reaction medium or is introduced by least one exchange process. It is advantageous for the cation that comes from the reaction medium to be selected from the group that is formed by the alkalines (except for lithium), the ammonium cation ($NH_{4+}$), nitrogen-containing organic cations (including alkyl ammoniums and aryl ammoniums), and phosphorus-containing organic cations (including alkyl phosphoniums and aryl ammoniums), and phosphorus-containing organic cations (including alkyl phosphoniums and aryl phosphoniums). M can also be a compensation cation that is introduced by post-synthesis ion exchange and is selected from the group that is formed by the cations of the elements of groups IA, IIA, and VIII of the periodic table, the cations of the rare earths (cations of elements having atomic numbers 57–71 inclusive), nitrogen-containing organic cations (including alkyl ammoniums and aryl ammoniums), and the ammonium cation;

m is the valence of cation M;

x is a number between 0 and 2 and preferably between 0.1 and 0.8;

y is a number that is greater than or equal to 0, preferably between 0 and 2; and most preferably y is greater than 0 and less than or equal to 2;

$\square$ represents an octahedral cavity.

The x-ray diffraction diagram of dioctahedral phyllosilicate 2:1 before bridging is characterized by the presence of the following lines:

a line that characterizes $d_{060}$, equal to:

→$1.49\pm0.01\times10^{-10}$ m (i.e., 0.149 nm) in the case where the dioctahedral phyllosilicate 2:1 contains an octahedral layer whose composition is the following Si , at least one 001 reflection such that $d_{001}$ is equal to $12.5\pm3\times10^{-10}$ m (i.e., 1.25 nm) depending on the nature of the compensation cation and its state of hydration at the moisture level in question.

Preferably, the fluorine content is such that the F/Si molar ratio is between 0.1 and 4, and between preferably 0.1 and 2.

Moreover, the dioctahedral phyllosilicate 2:1 has at least one rotation signal at the magic angle of $^{19}F$, which is determined and well-known to one skilled in the art. The chemical displacement of this signal also depends on the composition of the octahedral layer. Thus, said chemical displacement corresponds to a value of:

- −133 ppm (±5 ppm) in NMR with rotation at the magic angle of $^{19}F$, in the case where first neighbors of the fluorine (F) atom are two aluminum atoms; this corresponds to an octahedral layer whose composition is Si (Al$_2\square$);
- −108 ppm (±5 ppm) in NMR with rotation at the magic angle of $^{19}F$, in the case where the first neighbors of the fluorine (F) atom are two gallium atoms; this corresponds to an octahedral layer whose composition is Si (Ga$_2\square$);
- −118 ppm (±5 ppm) in NMR with rotation at the magic angle of $^{19}F$, in the case where the first neighbors of the fluorine (F) atom are one aluminum atom and one gallium atom; this corresponds to an octahedral layer whose composition is the following:
  Si (Ga, Al$\square$).

Said phyllosilicates can advantageously be synthesized in a fluoride medium in the presence of HF acid and/or another source of fluoride anions and at a pH of less than 9, and preferably between 0.5 and 6.5.

The preparation of these kinds of solids in a fluoride medium and their characterization are described in the references given hereinafter, the teaching of which should be considered part of this description: patent FR-A-2673930, a publication from the 202nd Session of the American Chemical Society (ACS) in New York in August 1991, the contents of which were published in Synthesis of Microporous Materials, Extended Clays and other Microporous Solids (1992), a report from the Academy of Sciences, Paris, Vol. 315, Series II, pp. 545–549, 1992.

The dioctahedral phyllosilicates 2:1 that are described above can advantageously contain fluorine and are bridged by, for example, a new process that includes the following stages:

the dioctahedral phyllosilicate 2:1, preferably in its ammonium form (NH$_{4-}$), is put into suspension in a solution of a surfactant whose concentration varies between 0.01 mol/liter and 1 mol/liter, and preferably between 0.05 and 0.07 mol/liter. The surfactants that can be used at this stage are anionic in nature, such as, by way of non-limiting examples, alkyl sulfates and alkyl sulfonates, or can be cationic in nature, among which can be cited tetralkylammonium halides or hydroxides such as cetyltrimethyl ammonium chloride or else geminal alkyl ammoniums.

By way of example, it is possible to use hexadecyltrimethyl ammonium bromide, ethylhexadecyldimethyl ammonium bromide, octadecyltrimethyl ammonium bromide, dodecyltrimethyl ammonium bromide, and didodecyldimethyl ammonium bromide. It is also possible to use other surfactants, such as, for example, triton X-100, polyethylene-oxide (POE).

After a contact time during which the medium is stirred, for example between 5 minutes and 12 hours and preferably between 15 minutes and 6 hours, and even more preferably between 15 minutes and 3 hours, the complex is filtered, then washed with distilled water, and finally dried under air or a cover gas, for example at a temperature of between 40 and 150° C., for a period of time of between 5 minutes and 24 hours and preferably between 30 minutes and 12 hours.

In the case where the phyllosilicate is not in ammonium form, it can first be run through any treatment that is known to one skilled in the art so as to obtain the majority of the dioctahedral phyllosilicate 2:1 in its ammonium form. By way of a non-limiting example of a treatment to accomplish this transformation, we can cite ion exchanges by aqueous solutions of an ammonium salt (ammonium nitrate and/or ammonium chloride).

the dioctahedral phyllosilicate 2:1, treated according to the process described in the previous step, is then brought into contact with a mixture that contains:

i) at least one primary amine such as RNH$_2$ or a secondary amine R'RNH, where R and R' are advantageously selected from the complex composed of the carbon-containing, alky, iso-alkyl, naphthenyl, and aromatic groups, which may or may not be replaced by other groups and which can contain 1 to 16 carbon atoms;

ii) at least one alkoxide of an element or a mixture of alkoxides, whereby the element is selected from the complex composed of the elements of groups IVB, VB, VIB, VIII, IB, and IIB, preferably silicon, aluminum, zirconium, titanium, and vanadium having the general formula M (OR)$_n$, where M is the element described above, n is the degree of valency of said element, and R is a group that is advantageously selected from the complex formed by the alkyl, iso-alkyl, naphthenyl, and aromatic groups, whether substituted or not. The various —OR groups may be the same or different, depending on the nature of the R group that is selected in the complex defined above.

The complex is allowed to remain in contact, preferably while being stirred, for a period of between 5 minutes and 12 hours and preferably between 5 minutes and 8 hours.

iii) the dioctahedral phyllosilicate 2:1 that is bridged in this way is then filtered and subsequently dried under air or a cover gas at a temperature of, for example, between 40 and 150° C., for a period of time of between 5 minutes and 24 hours and preferably between 30 minutes and 12 hours.

Said bridging process makes it possible to introduce simply and quickly pillars based on at least one oxide of the elements of groups IVB, VB, VIB, VIII, IB, IIB, IIA, and IVA, or a combination of said oxides, preferably based on least one of the compounds that is selected from the group formed by SiO$_2$, Al$_2$O$_3$, TiO$_2$, ZrO$_2$, and V$_2$O$_5$, or any combination of the latter. Said pillars are located in the inter-sheet space of the dioctahedral phyllosilicates 2:1 that are prepared in a fluoride medium.

The catalyst of this invention also optionally includes at least one usually amorphous or poorly crystallized matrix that is selected from the group that is formed by, for example, alumina, silica, magnesia, titanium oxide, zirconia, the phosphates of aluminum, titanium, or zirconium, boron oxide, combinations of at least two of these compounds, and alumina-boron oxide combinations.

The matrix is preferably selected from the group that is formed by silica, alumina, magnesia, silica-alumina combinations, and silica-magnesia combinations. The catalyst of this invention thus encompasses:

a) from 1 to 100% by weight, preferably 4 to 70% by weight, more preferably 10 to 60% by weight, and even more preferably 15 to 50% by weight of at least one dioctahedral phyllosilicate 2:1, which is preferably synthesized in a fluoride medium and bridged;

b) the makeup to 100% is composed of least one matrix as defined above.

The catalyst of this invention can be prepared by any of the methods that are known to one skilled in the art. One of the preferred methods in this invention consists in mixing the bridged dioctahedral phyllosilicate 2:1 in a moist aluminum gel for several tens of minutes, and then running the paste that is thus obtained through a die in order to form extrudates with a diameter of between 0.4 and 4 mm.

The catalyst according to the invention also encompasses at least one catalytic element having a hydro-dehydrogenating function, e.g., a metal. The hydro-dehydrogenating function is generally ensured by least one metal or metal compound of group VIII.

The group VIII metal is preferably selected from the group that is formed by iron, cobalt, nickel, ruthenium, rhodium, palladium, osmium, iridium, and platinum, and more preferably selected from the group composed of platinum, palladium, and nickel. In the preferred case where said metal is platinum or palladium, the content by weight is between 0.05 and 2%, and preferably between 0.1 and 1.5%. In the preferred case where said metal is nickel, the content by weight is between 0.1 and 10% and preferably between 0.2 and 6%. It is also possible to use a combination of several metals from group VIII and preferably from the group that is formed by nickel, platinum, and palladium.

The hydrogenating function as defined above can be introduced into the catalyst at any point in the preparation and by any technique that is known to one skilled in the art.

Said hydrogenating function can be introduced at the time when the dioctahedral phyllosilicate 2:1, which is synthesized in a fluoride medium and bridged, is mixed with the oxide gel that is selected as a matrix. Said function may be introduced by one or more ion-exchange operations on the calcined support that is composed of dioctahedral phyllosilicate 2:1, which is synthesized in a fluoride medium and is optionally bridged, and is dispersed in the selected matrix by means of solutions that contain the precursor salts of the selected metals from group VIII.

Said hydrogenating function can also be introduced onto the support (dioctahedral phyllosilicate 2:1+matrix) by any of the methods that are known to one skilled in the art, for example by least one dry impregnation of a solution that contains the precursor salts of the selected group VIII metals or by ion exchange. For example, said function can be introduced by means of anion exchange in the form of hexachloroplatinic acid in the case of platinum or in the form of chloride in the case of palladium.

Once the metal(s) has (have) been deposited, the catalyst may optionally undergo an activation treatment under air at high temperature, for example at a temperature of between 300 and 600° C., and then a treatment under hydrogen so as to obtain an active metal phase. The process of this treatment under hydrogen includes, for example, slowly raising the temperature under a stream of hydrogen until the maximum reduction temperature is reached, generally between approximately 300 and 700° C. and preferably between approximately 300 and 650° C., followed by holding at this temperature generally for a period of between 1 and 6 hours, preferably for 1.5 to 4.5 hours.

Isomerization (hydro-isomerization) takes place in at least one reactor. The temperature is between 150 and 350° C., preferably between 200 and 300° C., and the partial pressure of hydrogen is between 0.1 and 7 MPa and preferably between 0.5 and 5 MPa. The space velocity is between 0.2 and 10 liters of liquid hydrocarbon per liter of catalyst and per hour, and preferably between 0.5 and 5 liters of liquid hydrocarbon per liter of catalyst and per hour. The hydrogen/feedstock molar ratio at the inlet to the reactor is such that the hydrogen/feedstock molar ratio in the effluent leaving the reactor is generally greater than 0.01, preferably between 0.01 and 50, and more preferably between 0.06 and 20.

The following examples illustrate the invention without limiting its scope.

EXAMPLE 1

Preparation of a bridged dioctahedral phyllosilicate 2:1 (PDP1), which is of the beidellite type in sodic form and is part of the composition of catalyst C1 according to the invention.

For this preparation, to 36 grams of distilled water the following are added in succession and according to the 10 indications provided:

0.31 g of NaF salt (Prolabo) while being stirred moderately;

0.66 g of 40% HF acid (Fluka);

2.35 g of hydrated oxyhydroxide AlOOH (Catapal B Vista) while being stirred vigorously;

2.50 g of pulverulent $SiO_2$ oxide (Aerosil 130 from Degussa) while being stirred moderately.

The composition of the hydrogel that is prepared in this way, relative to one mole of $SiO_2$, is 1.0 $SiO_2$; 0.382 $Al_2O_3$; 0.177 NaF; 0.20 HF; 48 $H_2O$, or, in terms of molar ratio:

Si/Al=1.309
Na+/Si=0.177
F/Si=0.377
F/Si=0.20
$H_2O$/Si=48.

This composition does not take into account the water supplied by the aluminum source or the HF acid.

The hydrogel that is obtained in this way is aged for 4 hours at ambient temperature (20° C.) while being stirred moderately. The pH is then close to 5.

Crystallization is then carried out in a steel autoclave that is jacketed with a lining of polytetrafluorethylene (Teflon) having a capacity of 120 ml at 220° C. under autogenic pressure for a period of 168 hours without being stirred. The autoclave is then cooled to ambient air. The end-of-synthesis pH is approximately 4.

The product is then recovered, filtered, and washed copiously with distilled water. It is then dried at 40–50° C. for 24 hours. At the end of these 24 hours, the product obtained, at 50% relative humidity, is characterized by its x-ray diffraction diagram indicated below:

| $d_{hkl}(10^{-10}$ m) | 1/1o |
|---|---|
| 12.42 | 100 |
| 6.22 | 6 |
| 4.46 | 55 |
| 2.55 | 21 |
| 2.48 | 15 |
| 2.25 | 2 |
| 2.22 | 3.5 |
| 1.74 | 5 |
| 1.73 | 6 |
| 1.69 | 13 |
| 1.66 | 7 |
| 1.62 | 2 |
| 1.49 | 20 |

The fluorine content by weight of the phyllosilicate that is obtained is 3.15%. A signal at −133 ppm is present in the NMR spectrum that is obtained with rotation at the magic angle of $^{19}F$ of the phyllosilicate prepared according to this example.

The solid that is prepared in this way is then subjected to three successive ion-exchange operations using a solution of ammonium nitrate in order to obtain the $NH_4+$ form of the phyllosilicate. To do this, 10 g of the previously prepared phyllosilicate is put into suspension in 250 ml of a molar solution of ammonium nitrate and then stirred under reflux for 2 hours. The solid is then filtered and washed. This treatment cycle is repeated two more times. The solid that is obtained is then dried at 60° C. for 10 hours.

The dioctahedral phyllosilicate 2:1 that is prepared in this way is referred to as PD1. The latter will then undergo a bridging stage according to the procedure that is described below.

8 g of the dioctahedral phyllosilicate 2:1 that is thus prepared and referred to as PD1 and is in $NH_4$ form is put into suspension in 80 ml of a solution of hexadecyltrimethyl ammonium chloride (CTMA-C1) at a concentration of 0.1M. After being stirred for one hour at ambient temperature, the entire complex is filtered, washed twice with 200 ml of distilled water, and then dried at 60° C. for 8 hours. The PD1 sample, which has first been treated with CTMA, is put into suspension in a mixture composed of 4.48 g of octylamine ($C_8H_{17}NH_2$) and 60.32 g of ethyl tetraorthosilicate $Si(OEt)_4$. After being stirred for 30 minutes, the entire complex is filtered and then dried at 60° C. for a period of 8 hours. The sample is then calcined at 530° C. for 3 hours under air and then for 2 hours under pure oxygen.

The $d_{001}$ of the sample after calcination is $34.6 \times 10^{-10}$ m (3.46 nm), and its specific surface area is 390 m²/g.

The dioctahedral phyllosilicate 2:1 that is prepared in this way is called PDP1.

EXAMPLE 2

Preparation of the catalyst C1 (according to the invention)

The dioctahedral phyllosilicate 2:1 PP1 as described in Example 1 is mixed with type SB3 alumina supplied by the Condéa Company. The mixed paste is then extruded through a die with a diameter of 1.4 mm. The bridged clay content in the support (phyllosilicate+matrix) is 50% by weight.

Dry impregnation with a solution of platinum salt $Pt(NH_3)_4Cl_2$ is carried out in order to reach a platinum content on the support of 0.6% by weight. The catalyst that is obtained in this way is called C1.

EXAMPLE 3

Preparation of a bridged dioctahedral phyllosilicate 2:1 PDP2, which is a beidellite in ammonium form that is part of the composition of catalyst C2 according to the invention.

For this preparation, to 36 g of distilled water the following are added in succession and according to the indications given below:

0.385 g of NHF salt (Prolabo) while being stirred moderately;

0.312 g of 40% HF acid (Fluka);

2.71 g of hydrated oxyhydroxide AlOOH (Catapal B Vista) while being stirred vigorously;

2.50 g of pulverulent oxide $SiO_2$ (Aerosil 130 from Degussa) while being stirred moderately.

The composition of the hydrogel that is prepared in this way, relative to one mole of oxide $SiO_2$, is:

1.0 SiO2; 0.44 $Al_2O_3$; 0.25 $NH_4F$; 0.15 HF; 48 $H_2O$ or, in terms of molar ratio:

Si/Al=1.136

$NH_4^+$/Si=0.25

F/Si=0.40

HF/Si 0.15

$H_2O$/Si=48.

This composition does not take into account the water that is supplied by the aluminum source or the HF acid.

The hydrogel that is obtained in this way is aged for 4 hours at ambient temperature (20° C.) while being stirred moderately. The pH is then close to 5.

Crystallization is then carried out in a steel autoclave that is jacketed with a Teflon lining with a capacity of 120 ml at 220° C. under autogenic pressure for a period of 168 hours without being stirred. The autoclave is then cooled to ambient air. The end-of-synthesis pH is approximately 5.5.

The product is then recovered, filtered, and washed copiously with distilled water. It is then dried at 40–50° C. for 24 hours. At the end of these 24 hours, the product obtained, at 50% relative humidity, is characterized by its x-ray diffraction diagram.

| $d_{hkl}(10^{-10}$ m) | 1/1o |
|---|---|
| 10.87 | 73 |
| 5.32 | 12 |
| 4.46 | 100 |
| 2.58 | 30 |
| 2.56 | 43 |
| 2.2 | 46 |
| 2.1 | 77 |
| 2.0 | 77 |
| 1.69 | 11 |
| 1.49 | 22 |

The fluorine content by weight of the phyllosilicate that is obtained is 2.9%. A signal at −133 ppm is present in the NMR spectrum that is obtained with rotation at the magic angle of $^{19}F$ of the phyllosilicate that is prepared according to this example.

The dioctahedral phyllosilicate 2:1 that is prepared in this way is referred to as PD2. The latter will then undergo a bridging stage according to the procedure that is described below.

8 g of the dioctahedral phyllosilicate 2:1 that is prepared in this way and is referred to as PD2 and is in ammonium form is put in suspension in 80 ml of a solution of hexadecyltrimethyl ammonium chloride (CTMA-C1) at a concentration of 0.1M. After being stirred for one hour at ambient temperature, the entire complex is filtered, washed twice with 200 ml of distilled water, and then dried at 60° C. for 8 hours. The PD2 sample, which has first been treated with CTMA, is put into suspension in a mixture composed of 4.48 g of octylamine ($C_8H_{17}NH_2$) and 60.32 g of ethyl tetraorthosilicate $(Si(OEt)_4)$ and 2.96 g of aluminum isoproxide. After being stirred for 30 minutes, the entire complex is filtered and then dried at 60° C. for a period of 8 hours. The sample is then calcined at 530° C. for 3 hours under air and then for 2 hours under pure oxygen.

The $d_{001}$ of the sample after calcination is $31.2 \times 10^{-10}$ m (3.12 nm), and its specific surface area is 375 m²/g.

The dioctahedral phyllosilicate 2:1 that is prepared in this way is called PDP2.

EXAMPLE 4

Preparation of catalyst C2 (according to the invention).

Catalyst C2 is prepared according to the same procedure as the one described in Example 2, but this time using dioctahedral phyllosilicate 2:1 PDP2. The content by weight of bridged clay (bridged dioctahedral phyllosilicate 2:1) in the overall complex of the catalyst is 60%, and the palladium content that is introduced onto the support by dry impregnation is 0.55% by weight.

EXAMPLE 5

Preparation of catalyst C3 not according to the invention

In this example a dealuminated zeolite Y with a unit cell parameter of $24.42 \times 10^{-10}$ m (2.42 nm) is mixed with SB3 type aluminum supplied by the Condéa Company. The mixed paste is then extruded through a die with a diameter of 1.4 mm. The extrudates, which contain 40% by weight of zeolite Y, are then dry-impregnated with a solution of $Pt(NH_3)_4Cl_2$ in order to obtain a platinum content by weight of 0.5% by weight.

EXAMPLE 6

Catalytic evaluation of catalysts C1, C2, and C3 by hydro-isomerization of n-heptane Before they are catalytically evaluated, catalysts C1, C2, and C3 are subjected to calcination at 450° C. under dry air for 4 hours. The temperature is raised at a rate of 5° C./minute, and two plateaus of one hour apiece are maintained at 150° C. and 300° C.

The reduction of the metal phase is accomplished in situ in the catalytic reactor just before the test is carried out.

The reduction conditions for the three catalysts are as follows:

the temperature is raised at a rate of 7° C./minute to 150° C. under a stream of hydrogen, with a 30-minute plateau;

then the temperature is again raised at a rate of 7° C./minute to 300° C. under a stream of hydrogen, with a 30-minute plateau;

then, finally, the temperature is raised at a rate of 7° C./minute to 450° C. under a stream of hydrogen, with a 60-minute plateau.

The temperature is then reduced to the value of the reaction temperature, which is 250° C. The catalytic tests are carried out in a fixed-bed, gas-phase reactor. The molecule that is isomerized in the presence of hydrogen (hydro-isomerized) is n-heptane, and the molar ratio of hydrogen to n-heptane that is used in the various catalytic tests is 14. The space velocity, i.e., the mass of n-heptane that is injected per gram of catalyst and per hour, is adjusted so as to achieve a conversion of 75% by weight, which is the conversion level at which the comparisons of the selectivities of the catalysts will be made.

The products that are formed are either C1 to C6 cracking products or isomer products with 7 carbon atoms per molecule of n-heptane, or else aromatic products that result from the aromatization reactions of n-heptane.

The results that are obtained are summarized in the table below:

| Yields* (% by weight) | C1 (according to the invention) | C2 (according to the invention) | C3 (not according to the invention) |
| --- | --- | --- | --- |
| Cracking (%) | 7.5 | 10.6 | 28.6 |
| Isomerization (%) | 91.9 | 88.9 | 71.3 |
| Aromatization (%) | 0.6 | 0.5 | 0.1 |

*The conversion of n-heptane is 75% by weight.

This table shows that the use of a phyllosilicate according to the invention (catalysts C1 and C2) makes it possible to achieve an increase in isomerized products compared to a catalyst of the prior art.

What is claimed is:

1. A catalyst that contains at least one dioctahedral phyllosilicate 2:1 whose reticulate distance is equal to at least $26.5 \times 10^{-10}$ m and which includes pillars based on at least one oxide from the elements of groups IVB, VB, VIB, VIII, IB, IIB, IIA, IVA, or any combination of these oxides, and at least one element from group VIII wherein the phyllosilicate was synthesized in a fluoride medium in the presence at least one of HF acid and another source of fluoride anions, resulting in the incorporation of F in the catalyst.

2. A catalyst according to claim 1, wherein the dioctahedral phyllosilicate 2:1 has a reticulate distance that is at least equal to $28 \times 10^{-10}$ m.

3. A catalyst according to claim 2, wherein the dioctahedral phyllosilicate 2:1 has a reticulate distance that is less than or equal to $60 \times 10^{-10}$ m, the pillars are based on at least one oxide that is selected from the group consisting of $SiO_2$, $Al_2O_3$, $TiO_2$, and $V_2O_5$, and wherein the element from group VIII is nickel, platinum, or palladium, and wherein the catalyst comprises at least one matrix, and wherein the content of dioctahedral phyllosilicate 2:1 is between 4 and 70%.

4. A catalyst according to claim 1, wherein the pillars are based on at least one oxide that is selected from the group consisting of $SiO_2$, $Al_2O_3$, $TiO_2$, and $V_2O_5$.

5. A catalyst according to claim 1, comprising an element from group VIII selected from the group consisting of: Fe, Co, Ni, Ru, Rh, Pd, Os, Ir, and Pt.

6. A catalyst according to claims 5, wherein the element from group VIII is nickel, platinum, or palladium.

7. A catalyst according to claim 1 that also contains at least one matrix.

8. A catalyst according to claim 7, wherein the matrix is selected from the group consisting of alumina, silica, magnesia, titanium oxide, zirconia, the phosphates of aluminum, titanium, and zirconium, boron oxide, combinations of at least two of these compounds, and alumina-boron oxide combinations.

9. A catalyst according to claim 7, wherein the content of dioctahedral phyllosilicate 2:1 is between 4 and 70%.

10. A catalyst according to claim 1, wherein the dioctahedral phyllosilicate 2:1 has a reticulate distance that is at least equal to $30 \times 10^{-10}$ m.

11. A catalyst according to claim 10, wherein the dioctahedral phyllosilicate 2:1 has a reticulate distance that is equal to at least $30 \times 10^{-10}$ m and less than or equal to $60 \times 10^{-10}$ m, the pillars are based on at least one oxide consisting essentially of $SiO_2$, $Al_2O_3$, and $TiO_2$, wherein the element from group VIII is platinum, and wherein the catalyst comprises at least one matrix, the content of the dioctahedral phyllosilicate 2:1 being between 4 and 70% by weight of said catalyst.

12. A catalyst according to claim 1, wherein the at least one element from group VIII is platinum.

13. A catalyst according to claim 1, wherein the pillars are based on members consisting essentially of at least one oxide selected from the group consisting of $SiO_2$, $Al_2O_3$, and $TiO_2$.

14. A catalyst according to claim 1, produced by a process comprising:
(a) suspending the dioctahedral phyllosilicate 2:1 in a solution of a surfactant having a concentration of between 0.01 and 1 mol/liter;
(b) stirring the suspension, then filtering the suspension and washing the resultant filtered suspension with distilled water, and drying the washed suspension;
(c) when the phyllosilicate is not in an ammonium form in step (a), transforming the phyllosilicate to the ammonium form;
(d) contacting the ammonium form of the phyllosilicate with a mixture comprising at least one primary amine or a secondary amine, and at least one alkoxide of an element selected from the groups consisting of IVB, VB, VIB, VIII, IB and IIB;
(e) stirring the mixture and then drying the resultant bridged dioctahedral phyllosilicate 2:1.

15. A process of preparing a catalyst according to claim 1 comprising bridging a dioctahedral phyllosilicate 2:1, in a process comprising:
(a) suspending the dioctahedral phyllosilicate 2:1 in a solution of a surfactant having a concentration of between 0.01 and 1 mol/liter;
(b) stirring the suspension, then filtering the suspension and washing the resultant filtered suspension with distilled water, and drying the washed suspension;
(c) when the phyllosilicate is not in an ammonium form in step (a), transforming the phyllosilicate to the ammonium form;
(d) contacting the ammonium form of the phyllosilicate with a mixture comprising at least one primary amine or a secondary amine, and at least one alkoxide of an element selected from the groups consisting of IVB, VB, VIB, VIII, IB and IIB;
(e) stirring the mixture and then drying the resultant bridged dioctahedral phyllosilicate 2:1.

16. In a process comprising catalytically isomerizing a feedstock containing normal paraffins having 5 to 10 carbon atoms per molecule, the improvement wherein the catalyst is in accordance with claim 1.

17. A process according to claim 16 wherein the feedstock contains normal paraffins that have 5 to 8 carbon atoms per molecule.

18. A process according to claim 16, wherein isomerization is carried out at a temperature of between 150 and 350° C., a pressure of between 0.1 and 7 MPa, a space velocity of between 0.2 and 10 liters of liquid hydrocarbon per liter of catalyst and per hour, and a hydrogen/feedstock molar ratio at the inlet to the reactor such that the hydrogen/feedstock molar ratio in the effluent leaving the reactor is generally greater than 0.01.

19. A catalyst that contains at least one dioctahedral phyllosilicate 2:1 whose reticulate distance is equal to at least $20\times10^{-10}$ and that is less than or equal to $60\times10^{-10}$ m, and which includes pillars based on at least one oxide from the elements of groups IVB, VB, VIB, VIII, IB, IIB, IIA, IVA, or any combination of these oxides, and at least one element from group VIII wherein the phyllosilicate was synthesized in a fluoride medium in the presence at least one of HF acid and another source of fluoride anions, resulting in the incorporation of F in the catalyst.

20. A catalyst that contains at least one dioctahedral phyllosilicate 2:1 whose reticulate distance is equal to at least $26.5\times10^{-10}$ m and which includes pillars based on at least one oxide from the elements of groups IVB, VB, VIB, VIII, IB, IIB, IIA, IVA, or any combination of these oxides, and at least one element from group VIII, wherein the dioctahedral phyllosilicate 2:1 further comprises fluorine.

21. A catalyst according to claim 20, wherein the dioctahedral phyllosilicate 2:1 has a reticulate distance that is at least equal to $28\times10^{-10}$ m.

22. In a process comprising catalytically isomerizing a feedstock containing normal paraffins having 5 to 10 carbon atoms per molecule, the improvement wherein the catalyst is in accordance with claim 3.

23. In a process comprising catalytically isomerizing a feedstock containing normal paraffins having 5 to 10 carbon atoms per molecule, the improvement wherein the catalyst is in accordance with claim 6.

24. In a process comprising catalytically isomerizing a feedstock containing normal paraffins having 5 to 10 carbon atoms per molecule, the improvement wherein the catalyst is in accordance with claim 7.

25. In a process comprising catalytically isomerizing a feedstock containing normal paraffins having 5 to 10 carbon atoms per molecule, the improvement wherein the catalyst is in accordance with claim 8.

26. In a process comprising catalytically isomerizing a feedstock containing normal paraffins having 5 to 10 carbon atoms per molecule, the improvement wherein the catalyst is in accordance with claim 11.

27. In a process comprising catalytically isomerizing a feedstock containing normal paraffins having 5 to 10 carbon atoms per molecule, the improvement wherein the catalyst is in accordance with claim 14.

28. In a process comprising catalytically isomerizing a feedstock containing normal paraffins having 5 to 10 carbon atoms per molecule, the improvement wherein the catalyst is in accordance with claim 19.

* * * * *